United States Patent
Hegemann et al.

[19]

[11] Patent Number: 6,152,733
[45] Date of Patent: Nov. 28, 2000

[54] AUTOMATED HANDS FREE ORAL CLEANSING DEVICE WITH BITE BLOCK AND COMPUTER CONTROL

[75] Inventors: Kenneth J. Hegemann; Jay W. Hegemann, both of Escondido, Calif.; Robert E. Hegemann, Scottsdale, Ariz.

[73] Assignee: CRA Labs, Inc., Escondido, Calif.

[21] Appl. No.: 09/414,734

[22] Filed: Oct. 8, 1999

[51] Int. Cl.[7] ................................................. A61G 17/02
[52] U.S. Cl. ................................. 433/80; 433/82; 433/216
[58] Field of Search .................................. 433/80, 6, 216, 433/82, 93

[56] References Cited

U.S. PATENT DOCUMENTS

| | | | |
|---|---|---|---|
| 4,071,956 | 2/1978 | Andress | 433/216 X |
| 4,795,347 | 1/1989 | Maurer | 433/216 |
| 5,443,386 | 8/1995 | Vishup | 433/216 |

*Primary Examiner*—Nicholas D. Lucchesi
*Attorney, Agent, or Firm*—Richard R. Mybeck

[57] ABSTRACT

An automated hands-free personalized cleansing device for oral hygiene is described in which a robotic cleansing head is mounted for reciprocatable movement on a mounting base and is powered and controlled by a computer module to provide multiple movements of the brush portion thereof in and out, up and down and all about the user's oral cavity to provide ultimate cleansing of the teeth and gums and any openings found therein. In addition, the cleansing head is provided with a device to deliver fluid, with or without dentifrice, to preprogrammed locations within the oral cavity to treat and rinse the teeth and gums and a device to withdraw spent fluids from the oral cavity for delivery to suitable waste drain. Especially unique is the bite block which extends from the mounting base including a first portion for engagement between the rear-most teeth (upper and lower) of the user, and a second portion for engagement between the user's front teeth when bit upon. The bite block, which is customized for each user's mouth, and when inserted in the user's mouth and bitten into, serves to precisely orient to robotic cleansing head relative to that user's mouth and enables the robotic cleansing head to properly and accurately perform a pre-programmed mission of complete customized cleansing without any manual involvement by the user.

29 Claims, 11 Drawing Sheets

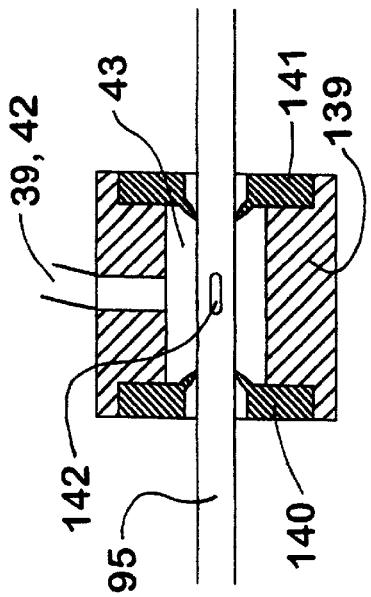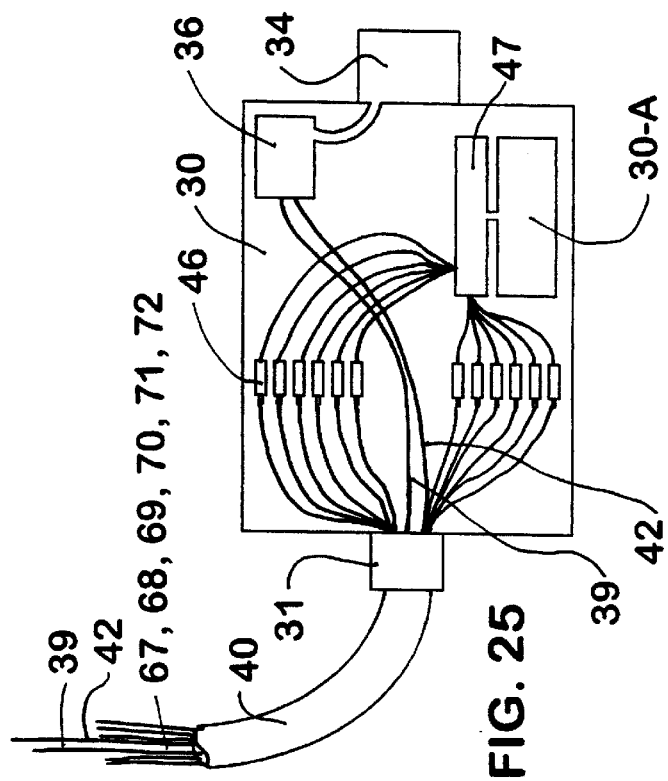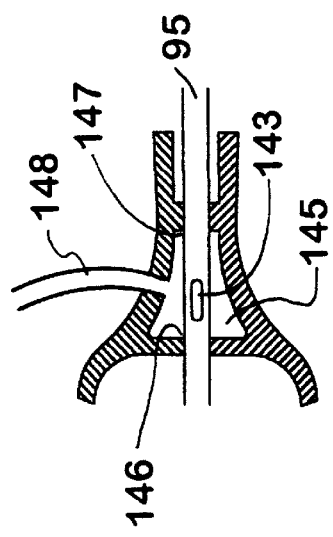

AUTOMATED HANDS FREE ORAL CLEANSING DEVICE WITH BITE BLOCK AND COMPUTER CONTROL

INTRODUCTION

The present invention relates to a novel automated hands-free tooth cleansing device and to the method of using the same in which a customized bite block is constructed to match the user's specific dental arrangement and thereafter guides a robotic cleansing head within the user's oral cavity to insure proper cleansing and stimulation to enhance healthy teeth and gums.

BACKGROUND OF THE INVENTION

Attempts to facilitate power-assisted dental appliances to enhance dental hygiene go back to the 19th Century when, inter alia, Case et al. received U.S. Pat. No. 600,243 for an Angle Attachment for Dental Handpieces as used in the Dentist's office.

More recent developments in power-driven toothbrushes and like devices to implement dental hygiene include multiple-function brushes as taught by Manning, U.S. Pat. No. 5,640,735; Berne, U.S. Pat. No. 5,365,624; Woog, U.S. Pat. No. 5,071,348; Crawford et al., U.S. Pat. No. 4,845,795 and Kudorko et al., U.S. Pat. No. 3,509,629, each of which use some form of power-drive. Computer assisted action is taught by Klinkhammer, U.S. Pat. No. 5,360,025; Loran et al., U.S. Pat. No. 4,941,826 and Barrett, U.S. Pat. No. 4,478,580.

Furthermore, over the last thirty to forty years, a diverse array of manual and electric toothbrushes, oral irrigators and flossers have enjoyed widespread commercial success. This attests to the important basic need to clean the teeth, gums and whole mouth area: a need made recently more acute by the introduction of refined sugars in many commercial and home-prepared foods. The human organism (fortunately or unfortunately), evolves physically at a much slower rate than socially, and no biological mechanism yet exists to deal with this onslaught; hence the particular importance of such cleaning devices.

Nonetheless, many problems exist with these devices, and for many people and in many situations, they are inadequate or unsuitable. Manual brushes, for instance, require the user to have a moderate degree of manual dexterity (at least) and the ability to firmly grasp the brush while moving it against the dental surfaces. The tiresomeness, difficulty and repetitiveness of manual brushing leads many to do less than is necessary; as is reported in *Consumer Reports*, September 1992, page 611: "People tend to brush for less than a minute. You need two or three minutes of manual brushing to do the job right," and so some teeth and gum surfaces may receive inadequate brushing or be missed altogether.

Electric toothbrushes, while requiring less physical effort, still require human skill and dexterity to achieve effective results and can pose an electrical hazard. They are more complicated than manual brushes and require more time in maintenance. Brushing too vigorously with electric brushes can irritate the gums or cause them to bleed excessively, possibly injuring the gums or eventually causing them to recede. Furthermore, bleeding can spread oral bacteria to the bloodstream, a risk for users with various health conditions including heart and immunity problems. Because of these problems, children must often be supervised when using electric toothbrushes, and children under the age of ten probably should not use them at all.

Oral irrigators (pulsating jets of pressurized water) and oral syringes (non-pulsating jets of pressurized water), while of benefit to users with crowns, implants, braces, or non-removable bridgework (for whom flossing or brushing is impractical or not possible), are also ineffective if the water jet is not correctly directed to the area where most needed for oral irrigation and stimulation. This is particularly a problem for an unsuspecting adult, teen or child if there is no safety mechanism to prevent higher pressure settings from remaining after a particular user has finished with the tool.

Additionally, flossing needs only be mentioned to note that it has found its best use as a cumbersome and sometimes painful way to remedy some of the deficiencies found in the other methods, such as brushing, particularly when attempting to reach areas between the teeth.

However, the fact of the matter is, that U.S. Government statistics show that nearly 75% of the adult population suffers from gum disease, which in turn can lead to tooth loss. The primary cause of gum disease is inadequate gum brushing and massage. The conclusion is supported in part by the fact that dental professionals (dentists and hygienists) are rarely affected by gum disease and/or tooth loss. Interestingly, they use the same toothbrushes as used by the general population. The reason for this vast difference in oral health can only be attributed to the fact that dental professionals (as part of their training) are taught exactly how to brush teeth and gums and most importantly, they comply with these cleaning measures every day. The logical conclusion is that gum disease is caused by human error.

The major shortcoming of manual and electric toothbrushes, oral irrigators and flossing is that they are all dependent on accurate human manipulation in order to achieve effective disease preventing results. The high incidence of gum disease in the general population provides convincing evidence that all present means of tooth and gum brushing are inadequate simply because they all depend on human skill. The present invention eliminates all need for human skill. None of the prior means and methods were capable of simple and safe operation; hygienic, comfortable, effective and error-free use; easy and inexpensive maintenance; and a cost-effective purchase price, for most people in most situations. Thus, there is a need for an improved device and the present invention fills this need by overcoming all of the foregoing deficiencies.

The present invention is presented as a means to remedy all the above-mentioned defects of past devices with the provision of a hands-free individually programmed dental care device which provides a safe, fast, comfortable and effective means of dental care and substantially eliminate gum disease for people of all ages, including those with implants, crowns, braces and bridgework, as well as people of limited dexterity, or other handicaps.

BRIEF SUMMARY OF THE INVENTION

The present invention provides a hands-free personalized dental cleaning appliance for cleaning teeth and gums having a bite block which is insertable into the user's mouth to establish the zero point for the cleaning operation, a robotic cleansing head attached to the bite block and including a tiltable brushing head and an adjustable brushing arm, the brushing head being rotatable while the brush arm wobbles, and a custom programmed computer module which activates both the brush head and the brush arm while simultaneously providing a controllable supply of customized dentrifice and/or mouthwash as required by the cleansing operation for the user's unique situation.

Accordingly, a prime object of the present invention is to provide a new and improved oral cleaning device including a bite block which accurately positions a multiple directional brush head and spray assembly in a pre-customized position and a computer control module to induce accurate robotic hands-free brushing, cleaning and massaging of the user's teeth and gums.

Another object of the present invention is to provide a new and improved device in which the parameters of a user's customized brushing needs are programmed and digitally stored in a computer control module for each discrete user and thereafter is selectively transmitted to a robotic cleansing head to enable the digital data to activate the movement of the robotic cleansing head in a pattern specific to the needs of that user while eliminating human error.

A still further object of the present invention is to provide a new and unique oral cleaning device which enables even the physically disabled to assure proper hygiene within his/her oral cavity including teeth, palates, gums, tongue and cheeks once the robotic cleansing head is properly installed by means of the bite block and without further hand contact.

These and still further objects as shall hereinafter appear are readily fulfilled by the present invention in a remarkably unexpected manner as will be readily discerned from the following detailed description of an exemplary embodiments thereof especially when read in conjunction with the accompanying drawing in which like parts bear like numerals throughout the several views.

BRIEF DESCRIPTION OF THE DRAWINGS

In the drawings:

FIG. 23 is an enlarged cross-sectional view of a portion of the brush arm of FIG. 22 showing the fluid exit port;

FIG. 24 is a cross-sectional view of a fluid seal and entry port generally for use in the cleansing head of FIG. 12;

FIG. 25 is a schematic view of the interior of the Computer Control Module of FIG. 1; and FIG. 26 is a cross-sectional view of the rotary power and fluid conduit of FIG. 1.

DESCRIPTION OF THE PREFERRED EMBODIMENT

The present invention relates to a new and useful automated hands free oral cleaning device comprising a unique coactive assemblage of several distinct sub-assemblies which will be herein described in detail.

In general, the present invention relates to an automated tooth and gum cleaning device which includes a unique bite block which positions a multiple directional brush head and spray assembly (herein called "robotic cleansing head"), and a computer control module to provide accurate robotic brushing, cleaning, massaging and flushing of the user's teeth and gums.

Figure 1:
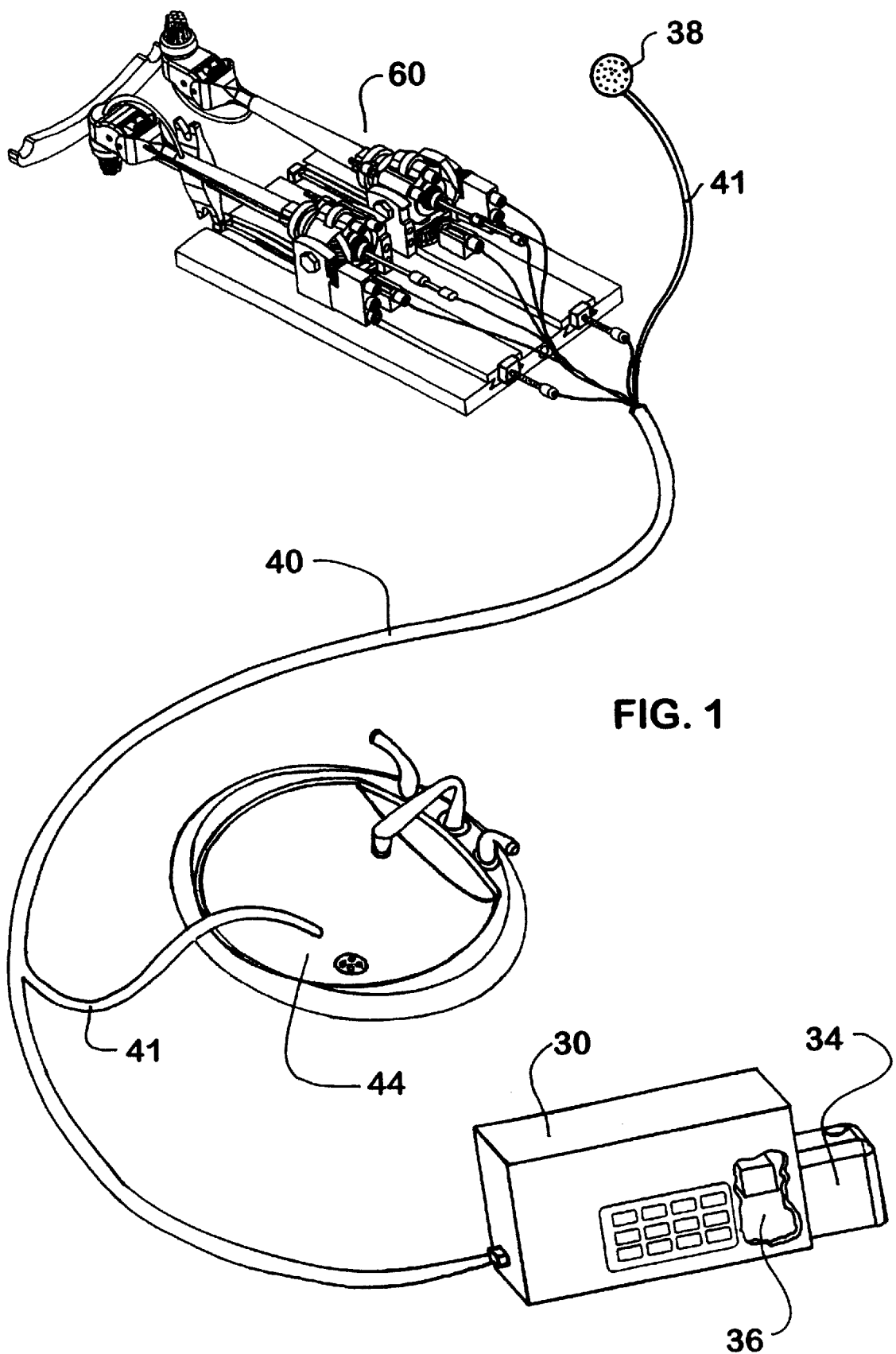
FIG. 1 is an isometric view of an exemplary embodiment of the present invention showing the interrelationship between robotic cleansing head assembly, the rotary power and fluid conductor, and the computer control module.

As shown in FIG. 1, the total assemblage is identified by the general reference 28 and comprises a computer control module 30, a fluid source 34, pump means 36, rotary power and fluid conduit 40, a drive motor 46, a bite block 50, and one or more robotic cleansing heads 60.

Figure 2:
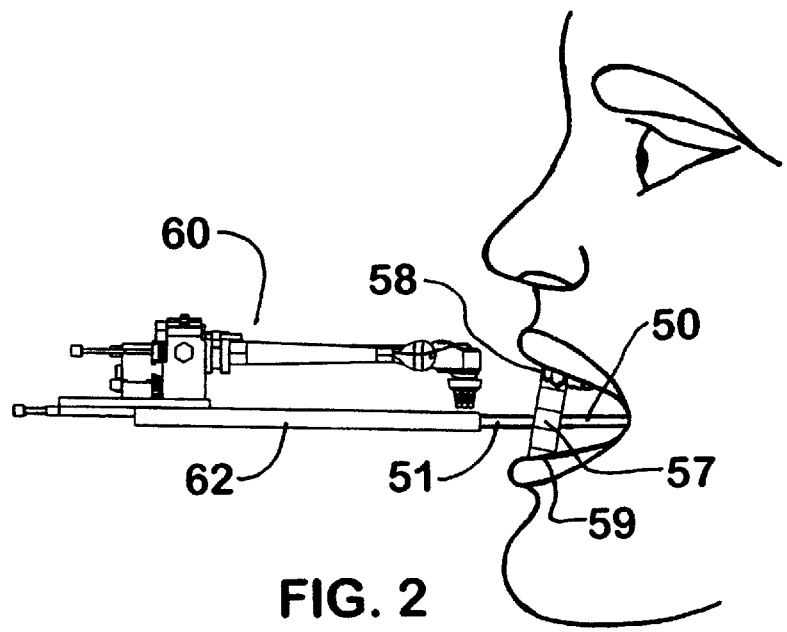
FIG. 2 is a side elevation view of the robotic cleansing head assembly operatively associated with the bite block to position the head assembly in the mouth of a user.
Figure 3:
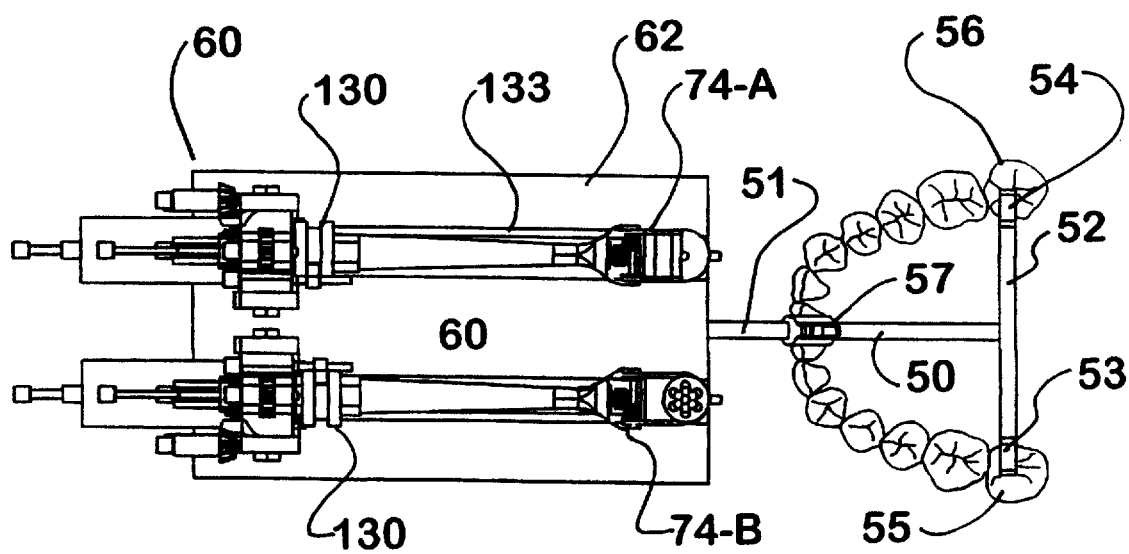
FIG. 3 is a plan view of FIG. 2 (with the human head removed) showing the bite block assembly and the robotic cleansing head positioned in the mouth of the user.
Figure 7:
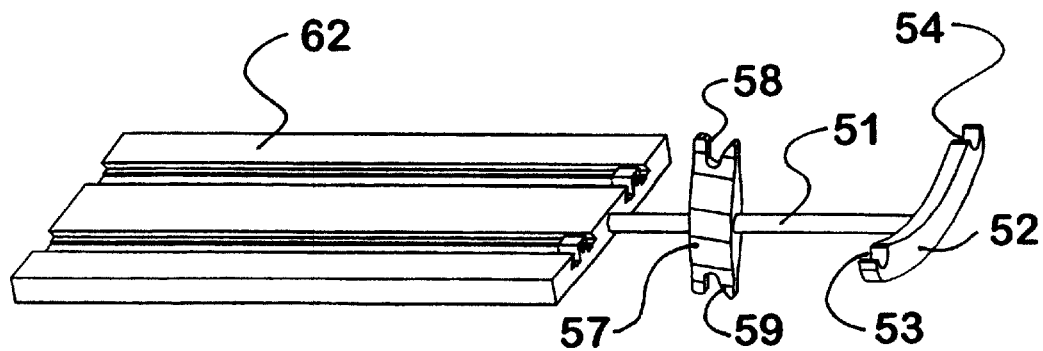
FIG. 7 is an isometric view of a bite block having a robotic cleansing head base attached thereto.
Figure 8:
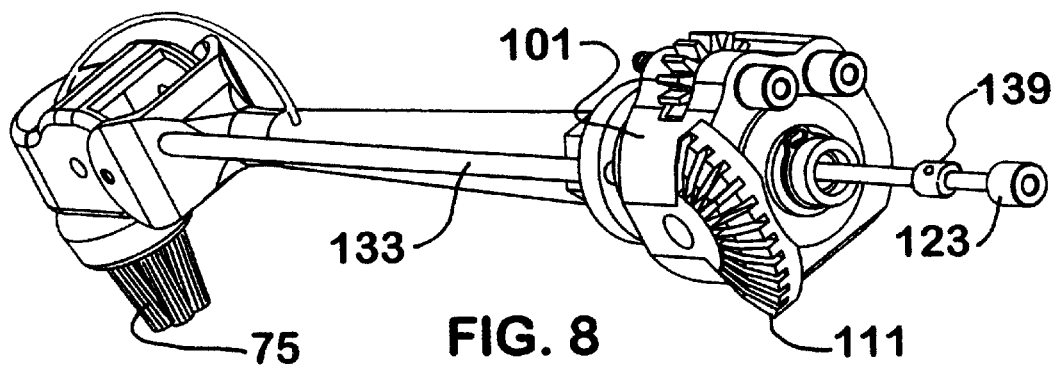
FIG. 8 is an isometric view of a single cleansing head.
Figure 9:
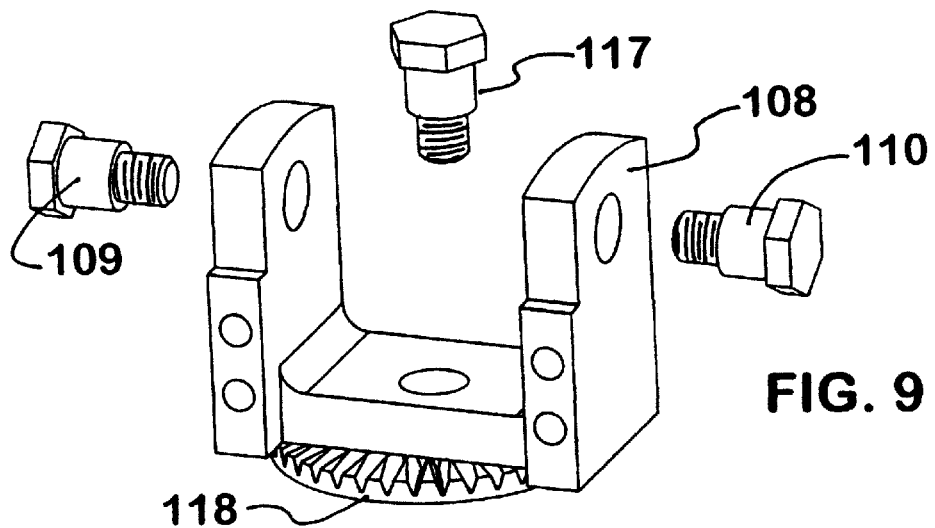
FIG. 9 is an exploded isometric view of the swivel gimbal retainer.
Figure 10:
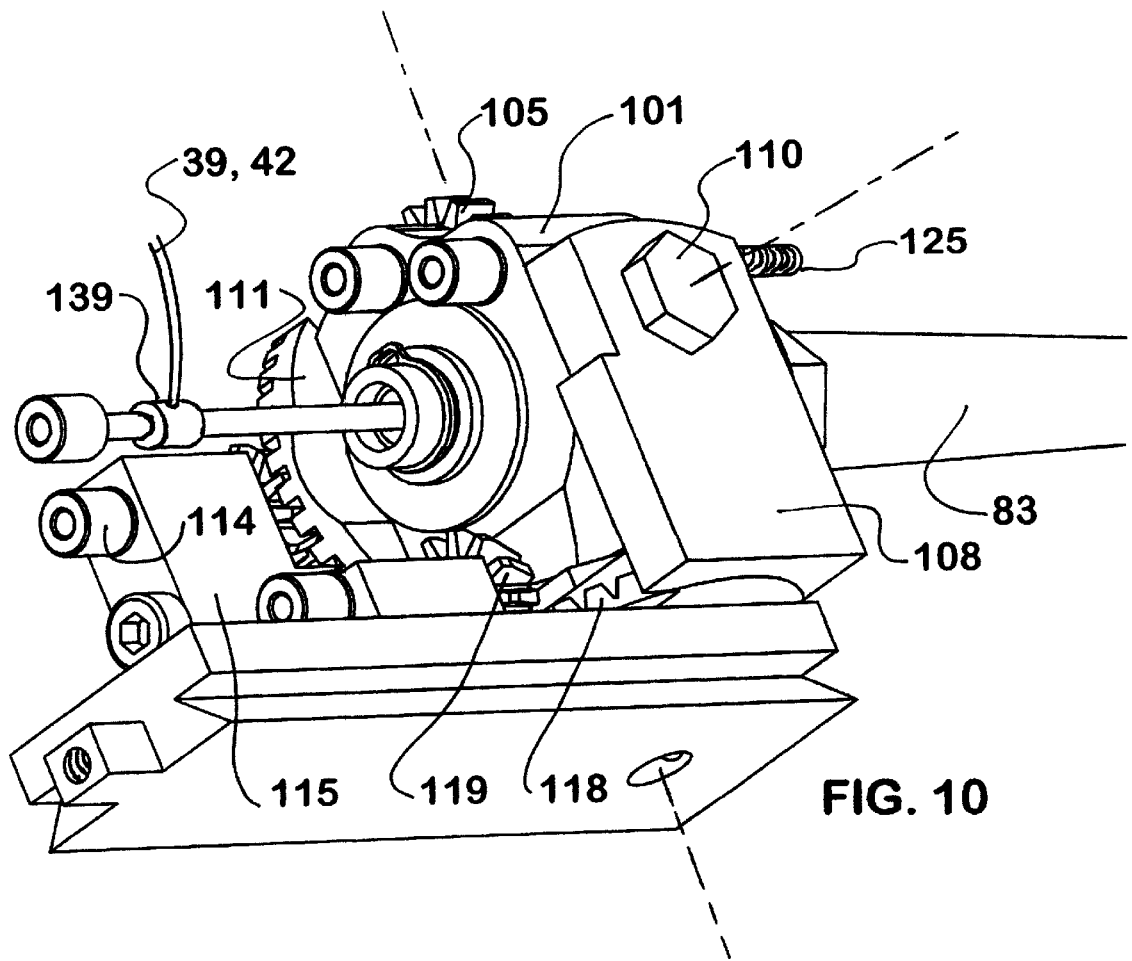
FIG. 10 is an enlarged isometric view of the dovetail slide having the cleaning head mounted thereto by means of the swivel gimbal retainer.
Figure 11:
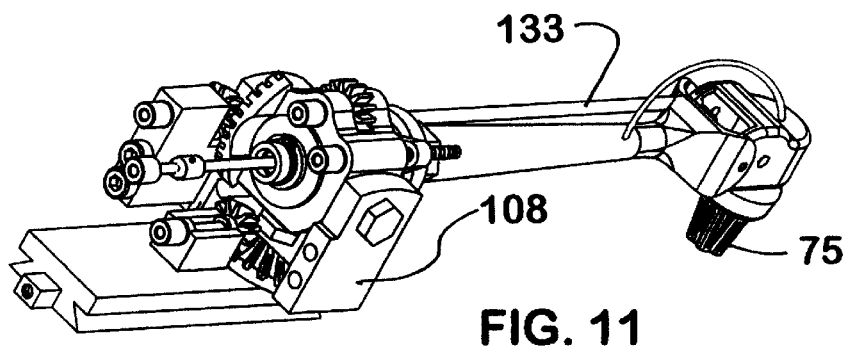
FIG. 11 is a rear isometric view of the cleaning head attached to the dovetail slide.

One important feature in the successful operation of the present invention, is obtained by the creation of a customized bite block to match the user's specific dental arrangement ("dental geography"). The bite block, once it has been customized by measuring the distance between the user's rearmost molars (side to side) and a comfortable frontal space, opening (top to bottom), is rigidly attached to the robotic cleansing head. Details of the bite block 50 are shown in FIGS. 2, 3, and 7. Next, the user's dental geography including such caps, crowns, missing teeth, gaps and other relevant parameters are programmed on a suitable disc and digitally stored in the computer control module 30 for each user of the device using conventional computer technology which need not be detailed here. At the time of use, the stored data for the specific user will be transmitted from the computer to the robotic cleansing head 60 where the transmitted data activates selective movements of the robotic cleansing head (including the brush and spray) in a pattern specific to the needs of that user.

As will further appear from the below detailed description of the several sub-assemblies hereof in relation to the accompanying drawings, the device will have either one or two brush arms, each of which is capable of rotating 360° within the brush support. The details of the brush mounting and support assembly are shown in FIGS. 4–6, 8, 10–14 and 16, while the interrelationship between the brush head as brush support is shown in FIGS. 17–22. The brush heads are replaceable when worn and are interchangeable with polishing heads when desired.

The multiple action of the brush head, that is, tilting in addition to or in lieu of rotating, is shown in FIGS. 2, 4, 5, 8, 14 and 16–19. A controlled water stream, preferably heated to about 90° F., accompanies the brushing to wash away the plaque dislodged from the teeth by the operation of the device as well as providing vital pulsating massage of the gums, particularly between the teeth. If dentrifice is desired, it will be injected with the water stream rather than applying it to the brush head. In addition to customized computer programming for each user of the device, each user will also have his/her own brush heads for obvious sanitary reason. The brush holder is further providing with reciprocatable linear movement into and out of the oral cavity in order to engage the rear most teeth and all of those inbetween. An important feature of the total assembly is the individually customized bite block to assure accurate and fixed position of the cleansing head assembly relative to the user's oral cavity. As will be described, the block engages both the upper and lower teeth and is customized for the individual user.

The master control (herein identified as "the control module 30") is conventional computer hardware and is operatively connected to the assembly. When the computer is activated, it commands the water spray and all movement (in and out, rotate and tilt) of the brush head assembly in response to its pre-program for the specific user, that is, the location, height, and width of the teeth and any gaps therebetween.

To recap, each unit is custom fit for specific user's mouths and will be defined by the Dentist or Dental Hygienist. The dental professional will make a full mouth impression and send that impression to the supplier of the device who will then pre-program the unit specific for the user's needs to insure that the brush bristles contact every surface of every tooth and provide 100% interproximal, gingival and subgingival contact while assuring that the brushing is not overly aggressive.

Each device further includes an oral irrigator that injects water, preferably with flavored dentifrice, through the bristles during the brushing action. Extra time for oral irrigation will be allowed interproximally to simulate flossing, and/or perio picks and/or proxy brushes. Drainage means are provided to withdraw all injected water from the user's mouth during operation in a user-friendly fashion. It will deliver the rinse water directly to the sink drain.

Note, that the device is always used with the bite block in the user's mouth to support the brush head assembly. Thus, the device operates entirely on its own and does not involve the user's hands once it is seated in the mouth.

Each of the several sub-assemblies will now be described in detail.

Returning to FIG. 1, which depicts an exemplary embodiment of the present invention, the embodiment generally comprises: a robotic cleansing head assembly 60, a computer control module 30, a fluid source 34, a pumping means 36, rotary power and fluid conduit 40 which interconnects fluid source 34 through pumping means 36 to the cleansing head assembly 60 and includes a suction mouth piece 38 connected to a waste disposal conduit 41 feeding to a suitable drain 44. The interaction of these various assemblies and their respective components will be hereinafter described in detail.

Robotic cleansing head assembly 60, as shown in FIGS. 2 and 3, includes a bite block 50, comprising an elongated connection rod 51, having a horizontally extending guide member 52, having a left bite pad 53 and a right bite pad 54, formed thereon in spaced relationship to each other at a distance substantially corresponding to the space between the user's rear molars 55, 56; and a vertically extending guide member 57, having an upper bite pad 58 and a lower bite pad 59, mounted thereupon to engage the user's upper and lower teeth, respectively and to maintain the mouth in a fixed open position.

As shown in FIGS. 2–3, the rear bite pads 53, 54 and the frontal bite pads 58, 59 are custom positioned and shaped to conform to the individual user's teeth and, as will appear, assure that the robotic cleansing head 60 is precisely positioned prior to and during use of the device to conform to the individual user's dental geography.

As shown in FIG. 3, rod 51 is insertable into base member 62 which supports one or more extendible, adjustable cleansing heads 60, as will now be described.

Figure 22:
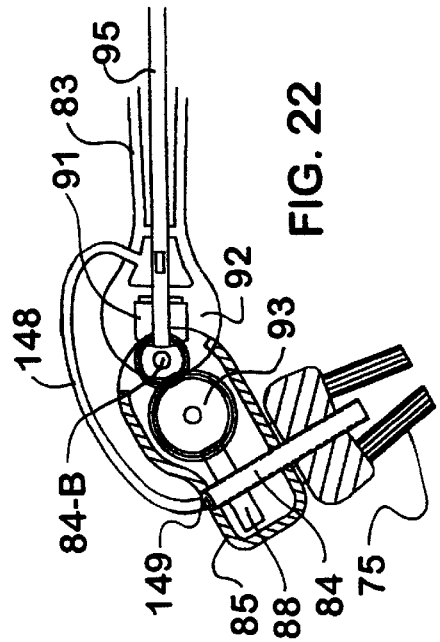
FIG. 22 is a fragmented cross-sectional view of the tilt adjustable brush of FIG. 17 showing a second alternative position.

The robotic cleansing head 60 requires several rotary input signals in order to function. To do this, several flexible shafts 67, 68, 69, 70, 71, and 72 are connected to key components of the cleansing head 60 as will be described in detail later. All of the flexible shafts 67, 68, 69, 70, 71, and 72 are grouped within the common rotary power conduit 40, which, as previously described, can be combined with fluid conductor 39 in a common conduit 40, as shown in FIG. 1 and FIG. 22, or routed independently of each other. A second fluid conductor 42, can likewise be combined with first conductor 39, and co-exist with the power transporting flexible shafts 67, 68, 69, 70, 71, and 72, all within the common conduit 40.

Referring now to FIG. 25, the fluid conductors 39, 42 and flexible shafts 67, 68, 69, 70, 71, and 72 within the fluid and rotary power conduit 40, enter the computer control module 30 at port 31. Each person using the device will have their own customized program stored in the computer 30. During use, computer 30 is powered on, and the customized information is sent to the drive motor controller 47, which then digitally directs the drive motors 46 to rotate in multiple combinations of clockwise and counterclockwise movements that are in turn sent to the robotic cleansing head 60 via the rotary power and fluid conduit 40. Each person using the device will also have a custom program to control fluid injection at desired times during use such as when the brush 75 is pointed directly between two teeth. This custom fluid pumping information is also sent from the computer 30 to the motor controller 47, which in turn sends the digital instructions to the fluid pump 36 and from the fluid pump 36 via conductor 40, up to the robotic cleansing head 60. It should be noted that computer 30, controller 47, fluid pump 36, drive motors 46 and the several required interface components are common items that are readily available from numerous sources.

Refer now to FIG. 7. The robotic cleaning head base 62 is rigidly attached to the bite block connection rod 51. Tooth contact pads 53, 54, 58 and 59 are secured to horizontal guide 52 and vertical guide 57, respectively, which are also rigidly attached to the bite block connecting rod 51 so that the robotic cleaning head base 62 is rigidly attached to the tooth contact pads 53, 54, 58 and 59 by way of the bite block connecting rod 51. When user bites down into the customized bite block pads 53, 54, 58 and 59, the robotic cleaning head 60 automatically becomes precisely positioned, every time the unit is used, relative to the user's mouth and that the all important and accurate starting point is always established.

Figure 4:
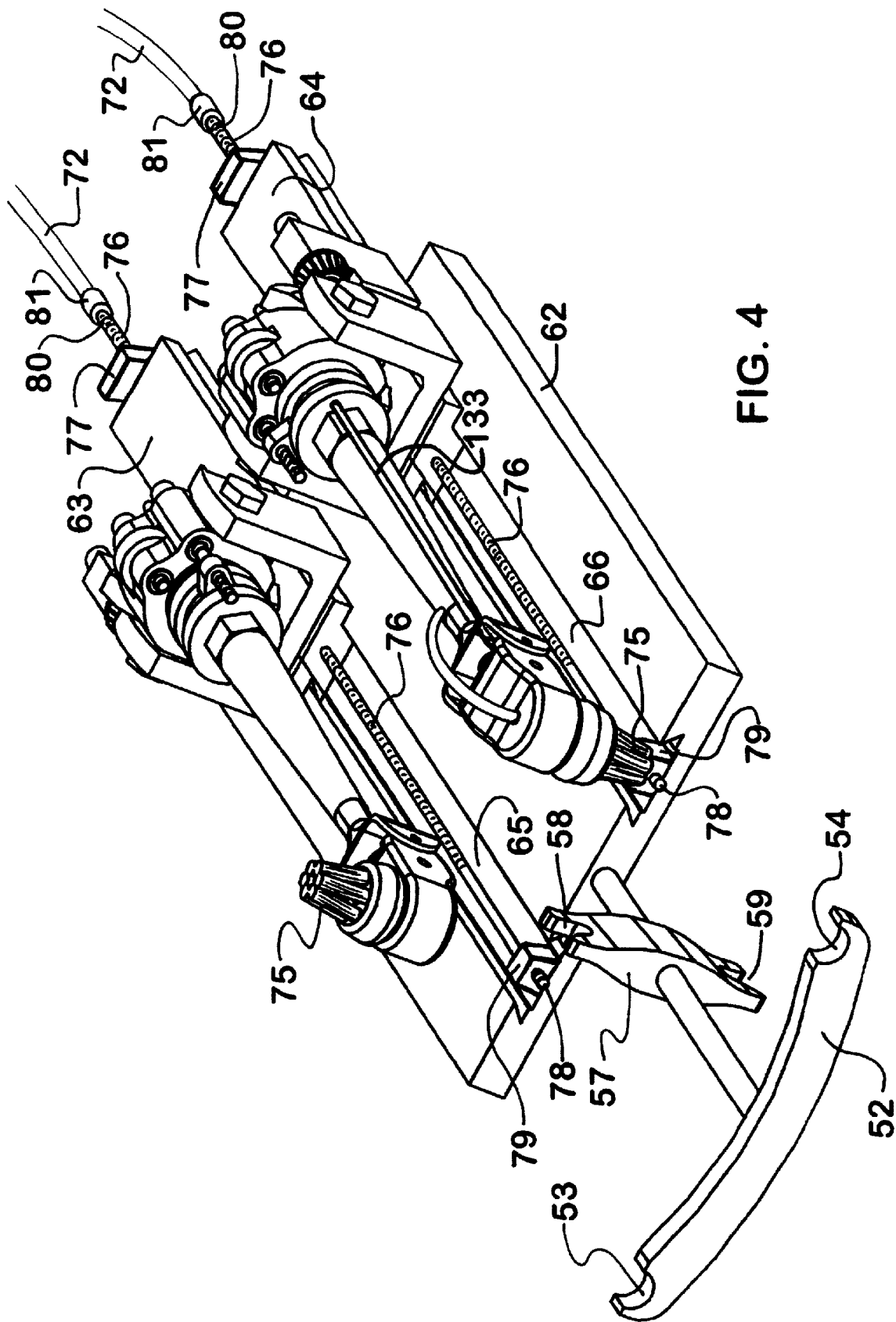
FIG. 4 is an isometric view of the robotic cleansing head and bite block assembly of FIG. 3 showing the cleaning heads in a retracted position.
Figure 5:
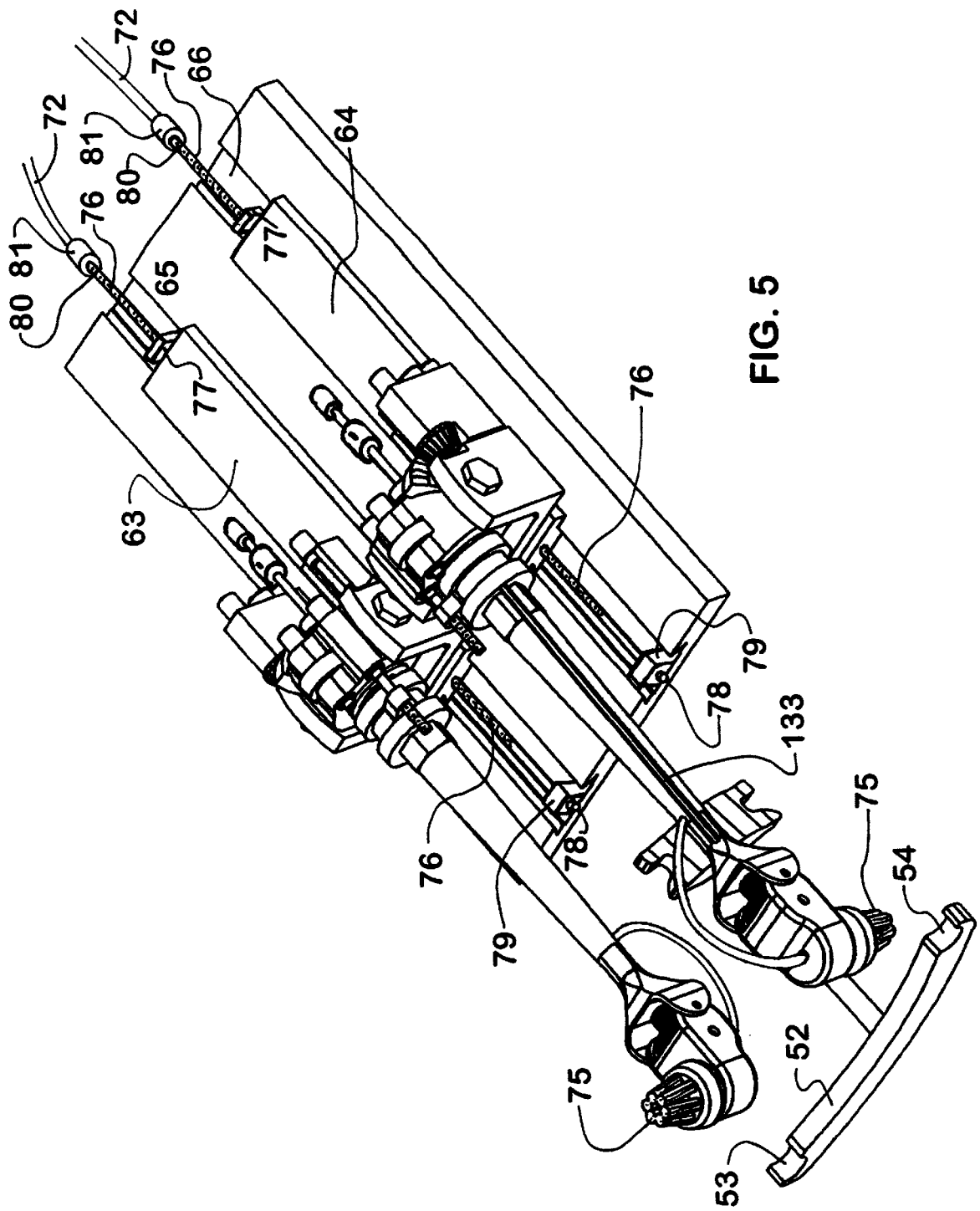
FIG. 5 is an isometric view of the assembly of FIG. 4 showing the cleaning heads in an extended position.
Figure 6:
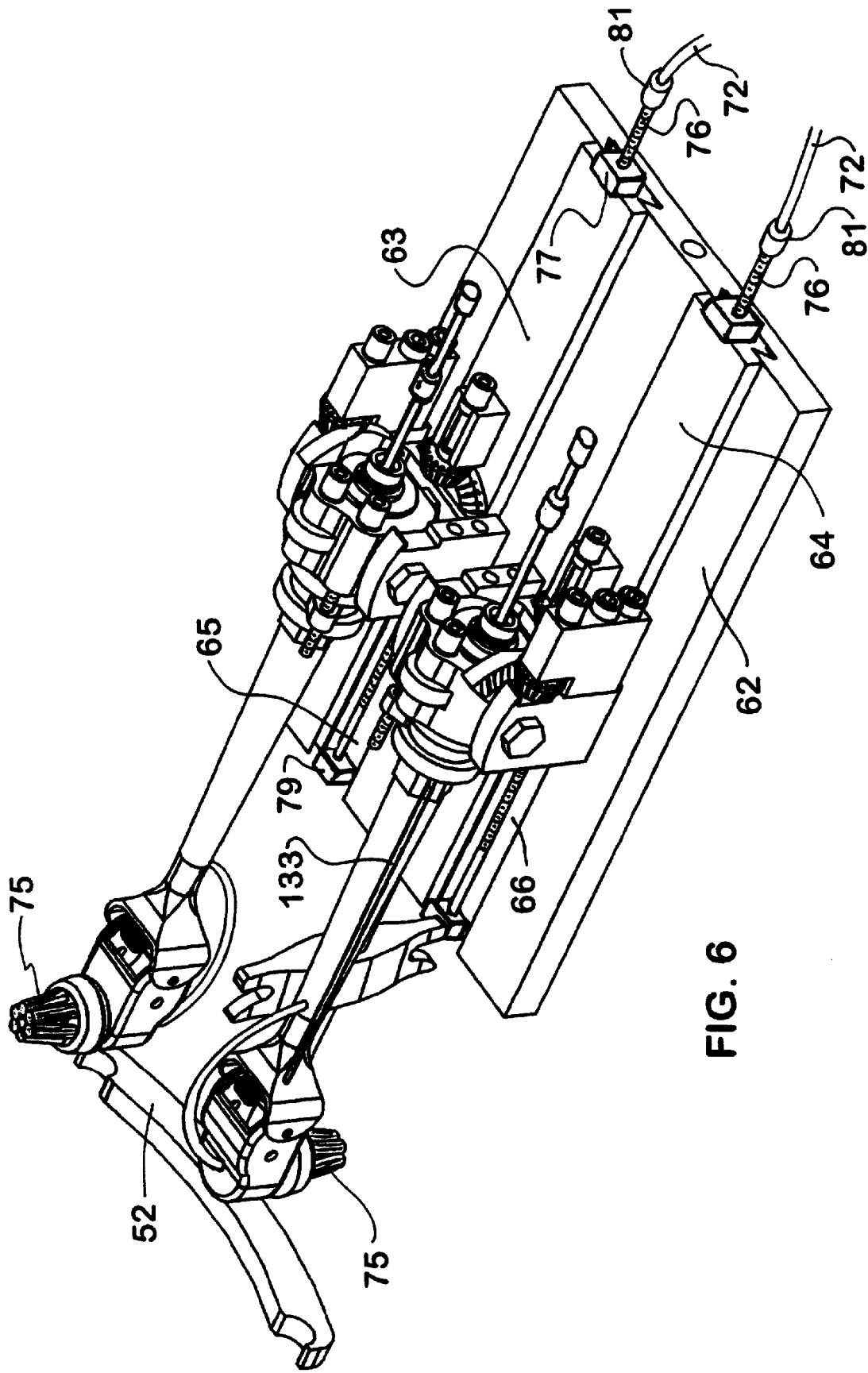
FIG. 6 is an isometric view of the assembly from the left rear of FIG. 5.

Referring now to FIGS. 4, 5 and 6, which illustrate robotic cleansing head assembly 60, two dovetail slides 63, 64 are movably connected to the robotic cleaning head base 62 in slots 65, 66, which enables slides 63, 64, to move linearly and independent of each other on the cleaning head base 62. This slide action provides in-out movement of the cleansing head 60 into the mouth and moves the brush 75 from tooth to tooth. A threaded rod 76 passes through and is able to rotate freely within the dovetail slides 63, 64, and the threaded rod 76 is rotationally engaged with an internally threaded nut 77, which is rigidly attached to the dovetail slides 63, 64. The front end 78 of the threaded rod 76 is supported by thrust bearing 79 to enable threaded rod 76 to rotate freely within thrust bearing 79. Simultaneously, thrust bearing 79 restricts threaded rod 76 from linear movement. The rear end 80 of threaded rod 76 has a coupling 81 that can receive rotary power from a flexible drive cable 72. When drive cable 72 rotates by means of a source that will be discussed later, clockwise or counterclockwise, the threaded rod 76 rotates in the same direction and the dovetail slide 63, 64 moves in and out respectively along the length of the corresponding slot 65, 66 in robotic cleaning head base 62.

Refer to FIGS. 3 and 17–22. Brushes 75, each are mounted on their respective brush heads 74A, 74B enter the mouth and work independent of each other and simultaneously clean and maintain the entire oral cavity according to a program that is customized for each person using the device. Each brush head 74A, 74B is programmed to follow predetermined paths around the varying shapes and contours of different teeth. Brushes 75 rotationally reciprocate approximately one and one half revolutions clockwise, then one and one half revolutions counterclockwise, etc. Each brush 75 is rigidly connected to a hollow shaft 84, which is in rotational contact with outer yoke 85 in socket at 86 and 87. A helical gear 88 is locked and positioned on hollow shaft 84 in cross mesh with helical gear 93, which in turn is engaged with spur gear 89 (See FIG. 18), and both gears 89, 93 are secured to shaft 84A. Spur gear 89 meshes with the spur/bevel combination gear 90 which is in turn in bevel mesh with bevel gear 91, which is rotationally locked onto hollow shaft 95. Spur/bevel combination gear 90, freely rotates on shaft 84B to provide appropriate mesh positioning of gears 89, 90 and 91 as well as providing a pivotal axis about which outer yoke 85 can rotate relative to inner yoke 92. When shaft 95 rotates in reciprocal clockwise and counterclockwise motion from a power source to be discussed later, it causes gear 91 to turn gear 90 which in turn causes gears 89 and 93 to rotate, causing gear 88 to rotate which causes brush 75 to move reciprocally. The position of outer yoke 85 changes relative to inner yoke 92 about their common axis which enables brush 75 to continue to rotate even as adjustments of outer yoke 85 are made relative to inner yoke 92 because spur gear 89 will move in planetary motion about spur/bevel gear 90 and remain engaged during any tilt adjustments of outer yoke 85. Inner yoke 92 is rigidly secured to brush arm 83 by suitable securing means 99.

Figure 12:
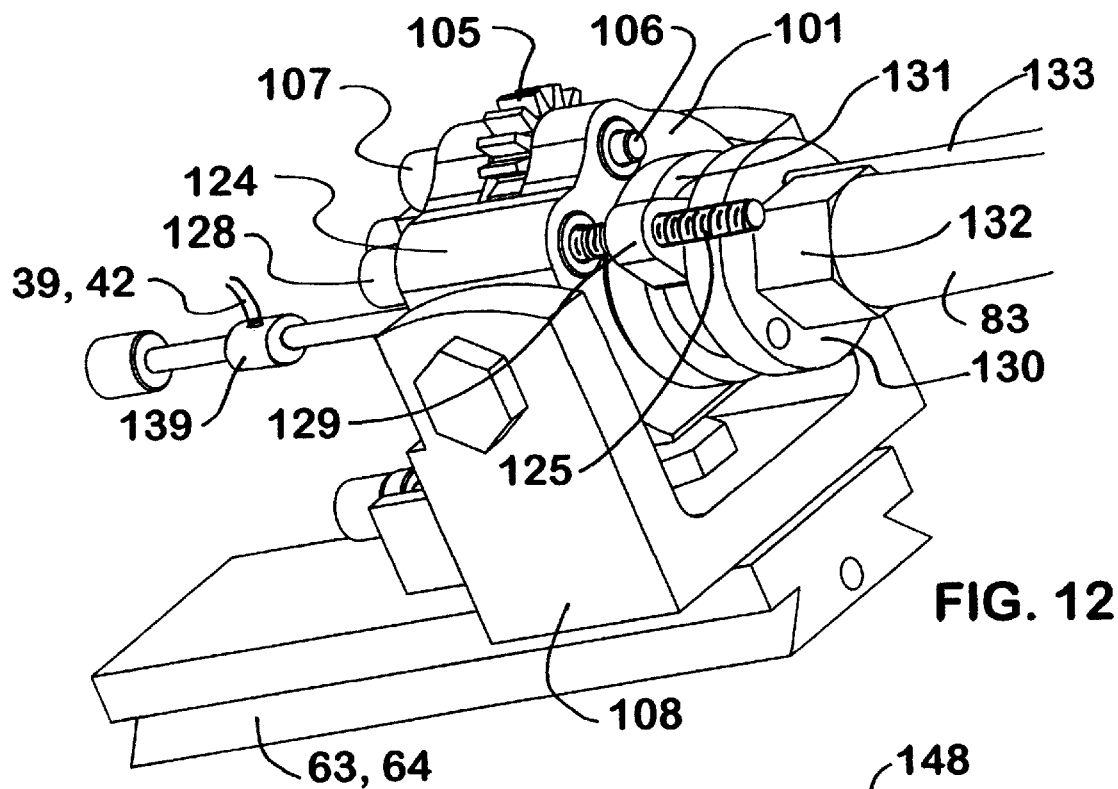
FIG. 12 is an enlarged isometric view of a cleaning head attached to the dovetail slide.
Figure 13:
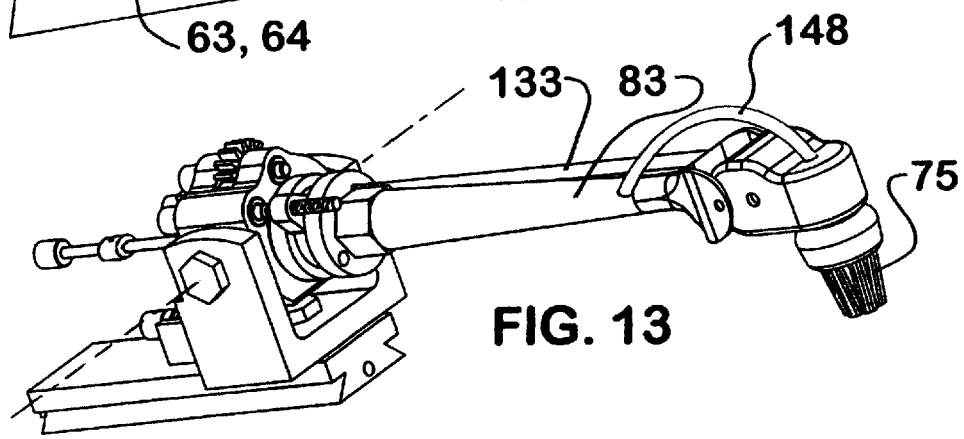
FIG. 13 is a front isometric view of a cleaning head of FIG. 11.
Figure 15:
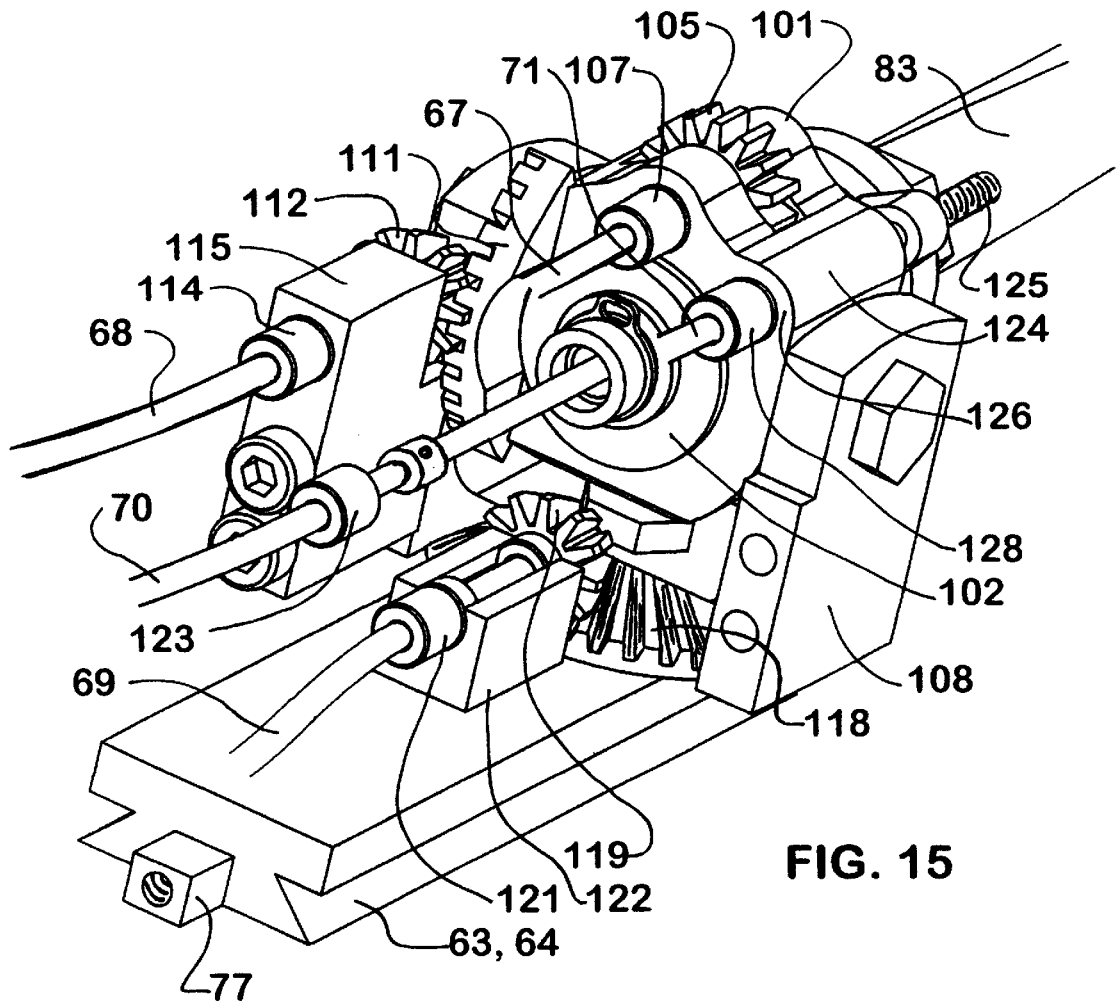
FIG. 15 is an enlarged isometric view of a cleaning head drive assembly embodying the present invention.
Figure 16:
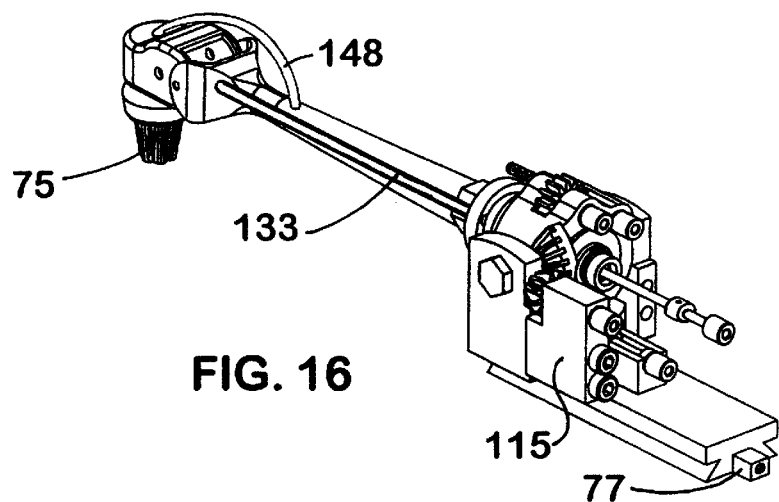
FIG. 16 is a rear isometric view of a cleaning head of FIG. 11 from the opposite side thereof.
Figure 17:
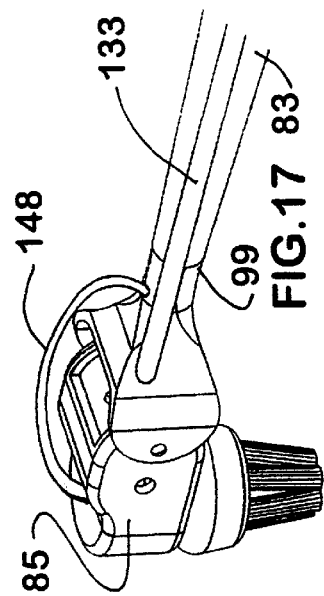
FIG. 17 is a fragmented isometric view showing the tilt mechanism of the adjustable brush.
Figure 18:
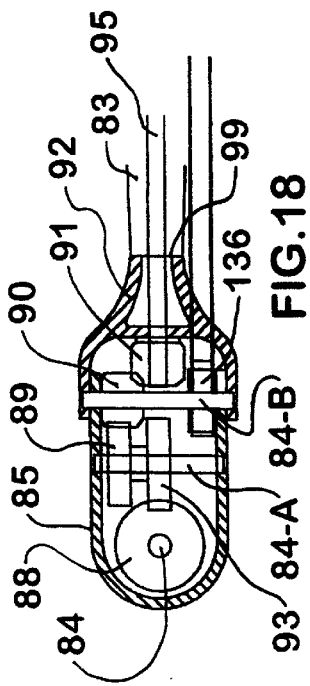
FIG. 18 is a top fragmented cross-sectional view of the tilt adjustable brush of FIG. 17.

Referring now to FIGS. 12 and 15, brush arm 83 passes through and is in 360-degree rotational contact within a gimbal 101 by means of bearings 102, 103. A spur gear 104 is centered and rigidly attached to brush arm 83 within the confines of gimbal 101. Spur gear 104 meshes with spur gear 105, which in turn is mounted on shaft 106 on which is mounted coupling 107. Flexible shaft 67 is engaged into coupling 107. When flexible shaft 67 rotates in response to its power source, to be discussed later, coupling 107, shaft 106, and spur gear 105 will rotate and cause spur gear 104 and brush arm 83 to also rotate. This potential 360-degree rotation allows brush 75 to reach any conceivable location within the oral cavity when working in conjunction with the other movements as described herein.

Referring now to FIGS. 8, 9, 10, 12, and 15, in which gimbal 101 is mounted in gimbal ring 108 using mounting bearing bolts 109, 110. This structure allows brush arm 83 to carry brush 75 to any vertical position as required to reach either upper or lower teeth. Bevel gear portion 11 is an integral part of gimbal 101 and meshes with bevel gear 112 as shown in FIG. 15. Bevel gear 112 is mounted to shaft 113, which in turn is attached to coupling 114. Shaft 113 is also in rotational contact within bearing block 115. Flexible shaft 68 is also attached to coupling 114. When flexible shaft 68 rotates clockwise or counterclockwise from a source that will be discussed later, coupling 114 rotates, which causes bevel gear 112 to rotate, which in turn causes bevel gear portion 111 and gimbal 101 to rotate, which in turn causes brush arm 83 to move vertically in an up and down motion. It should be noted that these movements can continue unaffected by any movement of dovetail slides 63, 64 within base member 62.

Gimbal ring 108 is in rotational contact with dovetail slides 63, 64 using bearing bolt 117. Bevel gear portion 118 is an integral part of gimbal ring 108 and is meshed with bevel gear 119. Bevel gear 119 in turn, is mounted to shaft 120 which is attached to coupling 121. Shaft 120 is in rotational contact within bearing block 122. Flexible shaft 69 is likewise attached to coupling 121 and when it rotates clockwise or counterclockwise from a source that will be discussed later, coupling 121 rotates, which causes bevel gear 119 to rotate, which in turn causes bevel gear portion 118 and gimbal ring 108 to rotate, which in turn causes gimbal 101 and brush arm 83 to move from side-to-side.

It should be noted that a combination of the up/down (vertical) and the side/side (horizontal) motions result in infinite positioning of brush 75 to reach any conceivable tooth location or configuration when used in conjunction with the other movements described herein, and most importantly, all movements can occur simultaneously or underneath each of other.

Hollow shaft 95 extends through the end of brush arm 83 into coupling 123. Flexible shaft 70 is attached to coupling 123 and when it reciprocates rotationally in response to the suitable power source, coupling 123 rotates and reciprocates, and brush 75 likewise rotates and reciprocates in response thereto as described earlier and is shown in FIG. 18.

Figure 14:
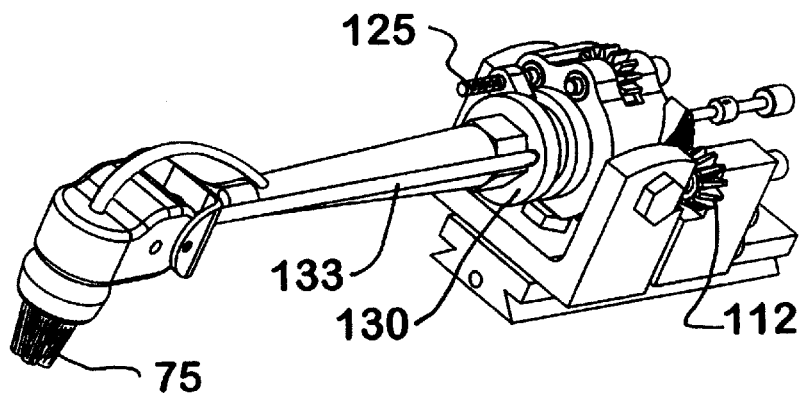
FIG. 14 is a front isometric view of the cleaning head of FIG. 11 taken from the other side of FIG. 13.
Figure 19:
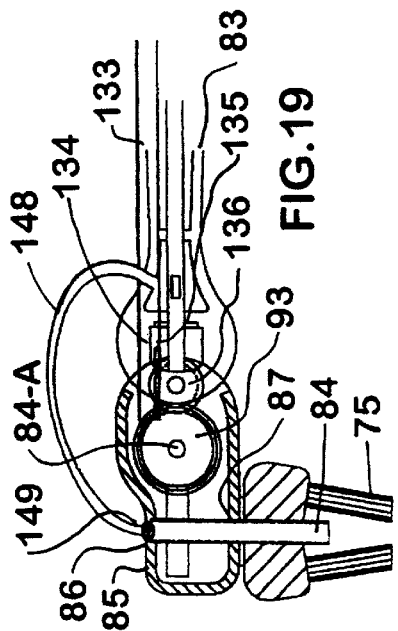
FIG. 19 is a side fragmented cross-sectional view of the tilt adjustable brush of FIG. 17.
Figure 20:
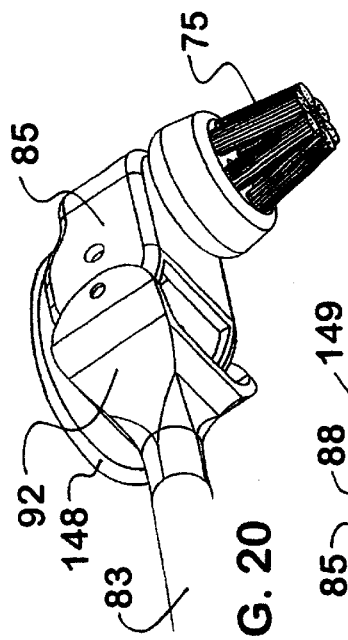
FIG. 20 is an enlarged isometric view of the tilt adjustable brush of FIG. 17 from the opposite side thereof.
Figure 21:
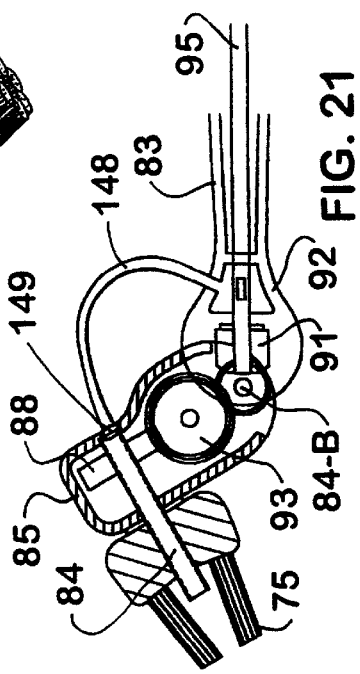
FIG. 21 is a fragmented cross-sectional view of the tilt adjustable brush of FIG. 17 showing a first alternative position.

Reverting to FIGS. 12, 14 and 15, bearing support boss 124 is another integral part of gimbal 101. Threaded shaft 125 is supported by bearings 126, 127 within bearing support boss 124. Coupling 128 is attached to the outer end of threaded shaft 125 which in turn, passes through internally threaded lug 129. Internal hex slide 130 slides linearly with respect to brush arm 83. Brush arm 83 is preferably round in cross-section except that portion 132 just outboard of gimbal 101 where the preferred cross-section of brush arm 83 is hexagonal. Internal hex slide 130 is thus able to slide axially along the outer periphery of brush arm 83 and still will rotate with brush arm 83. Internal hex slide 130 has a groove 131 defined therein in which internally threaded lug 129 can freely move. Internally threaded lug 129 comes into slide contact with internal hex slide 130 to prevent internally threaded lug 129 from rotating when threaded shaft 125 rotates. Flexible shaft 71 is connected to coupling 128 and when it rotates clockwise or counterclockwise in response to the power source, coupling 128 will rotate which causes threaded shaft 125 to rotate within internally threaded lug 129. This action enables lug 129 to move internal hex slide 130 along the hexagonal portion 132 of brush arm 83 and these slide adjustments will continue even as brush arm 83 rotates to any position within its 360 degree span of adjustment. Linkage rod 133 is rigidly attached to internal hex slide 130 as shown in FIG. 14 and, as shown in FIG. 19, the remote end 134 of linkage rod 133 has rack gear teeth 135, which mesh with spur gear 136 within outer yoke 85. Spur gear 136 is an integral part of outer yoke 85 and rotates with it. When linkage rod 133 moves in response to the linear movement of internal hex slide 130, the engagement with spur gear 136 causes outer yoke 85 to tilt to any desired position, even as brush arm 83 is making 360 degree rotational movements within gimbal 101.

Referring to FIGS. 1, 3, 15 and 26, each of the couplings 107, 114, 121, 123, 128 and 81 are capable of receiving flexible shafts 67, 68, 69, 70, 71 and 72 respectively. The six flexible shafts 67, 68, 69, 70, 71 and 72 are repeated for each of the two cleansing heads 60A and 60B. When two heads are used, all of the flexible shafts (twelve in all), can come together in a single conduit 40, which carries the twelve flexible cables to the drive motors 46 located in the computer control module 30.

It is anticipated that when produced, the device 28 which is the object of this invention, will likely be available only from dental practitioners, where the dentist will create a full impression of patient's teeth and gums and with the impression negative, create a positive model. Technicians will then study the model and create a customized program of brushing and water jet perfection to match the model using Computer Aided Design. The data is imprinted on a disc and stored in computer 30 for retrieval when needed. In use, the patient will place the bite block 50 into his/her mouth and bite onto the several bite contact pads 53, 54, 58, and 59. The robotic cleansing heads 60A, 60B are thus properly positioned at the correct starting point for that user's mouth. Computer 30 is placed into its run mode and the customized program information is fed to the motor control unit 47, which is electrically connected to drive motors 46. Drive motors 46 respond to the motor control units instructions and deliver customized reciprocating and rotary motion to the robotic cleansing heads via flexible shafts 67, 68, 69, 70, 71, and 72 within single conduit 40. Computer 30 is also programmed to provide a customized water program for flushing between teeth and into gum pockets according to the perceived needs of each user of the device. With computer 30 powered up, digital signals are sent from computer drive 30A to control module 47 and from there to fluid pump 36. Water is drawn from reservoir 34 into fluid pump 36, and is then forced through fluid conductors 39, 42. Fluid conductors 39, 42 join and remain adjacent to each other within the rotary power and fluid conduit 40 on the way up to robotic cleansing head 60 as shown in FIG. 12. At the robotic cleansing head 60, fluid conductor 42 enters a rotary coupling 139 as shown in FIG. 24. While hollow shaft 95 rotates to drive brush 74, rotary coupling 139 does not rotate. Water enters rotary coupling 139 through fluid conductor 39 and accumulates in chamber 43. Rotary coupling 139 is provided with end seals 140, and 141 which entrap water within fluid chamber 43. Hollow shaft 95 is plugged on both ends and has an opening or notch 142 defined thereupon. Water enters hollow shaft 95 at opening 142 to fill hollow shaft 95. At the brush end of hollow shaft 95 (See FIGS. 22 and 23), hollow shaft 95 has another opening 143 therethrough which water exits hollow shaft 95 and fills chamber 145. Chamber 145 is sealed on both ends with rotary seals 146, 147. Flexible fluid conductor 148 originates within chamber 145 and connects the end of hollow shaft 95 to a rotary connector 149 on the top of outer yoke 85. As the opposite end of hollow shaft 84 is opened, water will jet directly into the oral cavity in the precise location as directed by the customized program within the computer 30. Referring back to FIG. 1, a return fluid suction device 38 is placed in user's mouth during operation of the device. Return fluid conductor 41 is also disposed within conduit 40, adjacent to and independent of the other fluid conductors 39, 42 and the flexible shafts 67, 68, 69, 70, 71 and 72 and all remain within conduit 40 until the return fluid conductor 41 departs to deliver the return fluids directly into drain basin 44.

From the foregoing, the construction and operation of the automated tooth and gum cleaning device concept will be readily understood and further explanation is believed to be unnecessary. However, since numerous modifications and changes will readily occur to those skilled in the art, it is not desired to limit the invention to the exact constructions shown and described. Accordingly, the aim in the appended claims is to cover all such modifications and changes as may fall within the true spirit and scope of the invention.

Accordingly, what is claimed is:

1. A customizable automated cleansing device for oral cavities comprising: a robotic cleansing head assembly; a computer control module; a fluid source; a fluid conduit operatively connected between said fluid source and said cleansing head; a power conduit operatively connected between said computer control module and said robotic cleansing head; and a bite block adapted to be statically positioned in said oral cavity to operatively guide said robotic cleansing head into, out of and about said oral cavity to interact with the gums and teeth in said oral cavity and remove all debris therefrom.

2. A device according to claim 1, having pump means operatively interposed between said fluid source and said robotic cleansing head assemblies in said fluid conduit.

3. A device according to claim 2, in which said fluid source comprises water.

4. A device according to claim 3, in which said water is warmed to about 90° F.

5. A device according to claim 3, in which said fluid source further comprises a water soluble dentrifice.

6. A device according to claim 5, in which said fluid source is warmed to about 90° F.

7. A cleansing device according to claim 1, in which said robotic cleansing head assembly comprises a linearly actuatable brush holder, base means for supporting said brush holder and enabling the movement of said brush holder relative thereto; and at least one brush means secured to said brush holder and moveable in response thereto into, out of and about an oral cavity to be cleaned.

8. A cleansing device according to claim 7, comprising a first and a second brush means.

9. A cleansing device according to claim 8, in which said first brush means and said second brush means are linearly actuatable independently of each other.

10. A cleansing device according to claim 8, in which said first brush means and said second brush means are rotationally actuatable independently of each other.

11. A cleansing device according to claim 7, in which said brush means includes handle means attachable to said brush holder at the proximal end thereof, and moveable in response thereto and brush hairs attachable to said handle means at the distal end thereof.

12. A cleansing device according to claim 11, in which said handle means includes brush hair base means pivotally attached and rotatable relative to said handle means.

13. A cleansing device according to claim 12, in which said handle means further comprises means for tilting said brush hair base means upwardly and downwardly within the vertical plane of said handle means.

14. A cleansing device according to claim 1, in which said bite block comprises an axially extending connection rod having a first positioning device secured to the distal end thereof and dimensioned to conform to the space between the user's rear teeth, said first device having first dental pads for engaging a user's rear tooth on the right and second dental pads for engaging a rear tooth on the left; and a second positioning device secured to said connection rod in spaced relationship to said first positioning device and having a first and a second dental pad disposed respectively on the ends thereof for engaging the upper and lower front teeth of the user when the user bites thereupon to hold user's oral cavity in an open position and precisely orient said robotic cleansing head relative to said oral cavity.

15. A cleansing device according to claim 14, in which said robotic cleansing head assembly comprises a linearly actuatable brush holder, base means for supporting said brush holder and enabling the movement thereof relative thereto, at least one brush means secured to said brush holder and moveable in response thereto into, out of and about said oral cavity on an axis parallel to that defined by said connection rods and said first and said second positioning devices in their fixed relationship to said base means.

16. A cleansing device according to claim 15, in which said cleansing head assembly further comprises a first and a second brush means operative independently of each other.

17. A cleansing device according to claim 1 further comprising means for automatically extracting and discarding all said debris from all said oral cavity.

18. A customizable automated cleansing device for oral cavities comprising: a robotic cleansing head assembly; a computer control module; a power conduit operatively connected between said computer control module and said robotic cleansing head; and a bite block adapted to be statically positioned in said oral cavity to operatively guide said robotic cleansing head into, out of and about said oral cavity for interaction with the gums and teeth in said oral cavity and to remove all debris therefrom.

19. A cleansing device according to claim 18, in which robotic cleansing head assembly comprises a linearly actuatable brush holder, base means for supporting said brush holder and enabling the movement of said brush holder relative thereto; and at least one brush means secured to said brush holder and moveable in response thereto into, out of and about an oral cavity to be cleaned.

20. A cleansing device according to claim 19, comprising a first and a second brush means.

21. A cleansing device according to claim 20, in which said first brush means and said second brush means are linearly actuatable independently of each other.

22. A cleansing device according to claim 20, in which said first brush means and said second brush means are rotationally actuatable independently of each other.

23. A cleansing device according to claim 19, in which said brush means includes handle means attachable to said brush holder at the proximal end thereof, and moveable in response thereto and brush hairs attachable to said handle means at the distal end thereof.

24. A cleansing device according to claim 23, in which said handle means includes brush hair base means pivotally attached and rotatable relative to said handle means.

25. A cleansing device according to claim 24, in which said handle means further comprises means for tilting said brush hair base means upwardly and downwardly within the vertical plane of said handle means.

26. A cleansing device according to claim 18, in which said bite block comprises an axially extending connection rod having a first positioning device secured to the distal end thereof and dimensioned to conform to the space between the user's rear most teeth, said first device having first dental pads for engaging a rear tooth on the right and second dental pads for engaging a rear tooth on the left; and a second positioning device secured to said connection rod in spaced relationship to said first positioning device and having a first and a second dental pad disposed respectively on the ends thereof for engaging the upper and lower front teeth of the user when the user bites thereupon to hold user's oral cavity in an open position and precisely orient said robotic cleansing head relative said oral cavity.

27. A cleansing device according to claim 26, in which said robotic cleansing head assembly comprises a linearly actuatable brush holder, base means for supporting said brush holder and enabling the movement thereof relative thereto, at least one brush means secured to said brush holder and moveable in response thereto into, out of and about said oral cavity on an axis parallel to that defined by said connection rods and said first and said second positioning devices in their fixed relationship to said base means.

28. A cleansing device according to claim 27, in which said cleansing head assembly further comprises a first and a second brush means operative independently of each other.

29. A cleansing device according to claim 18 further comprising means for automatically extracting and discarding all said debris from all said oral cavity.

* * * * *